(12) United States Patent
Rousu et al.

(10) Patent No.: US 11,202,651 B2
(45) Date of Patent: Dec. 21, 2021

(54) MEDICAL BALLOON WITH ENHANCED FOCUSED FORCE CONTROL

(71) Applicant: C.R. Bard, Inc., Tempe, AZ (US)

(72) Inventors: Corey Rousu, Cave Creek, AZ (US); Karen DiClaudio, Chandler, AZ (US)

(73) Assignee: C.R. Bard, Inc., Tempe, AZ (US)

( * ) Notice: Subject to any disclaimer, the term of this patent is extended or adjusted under 35 U.S.C. 154(b) by 442 days.

(21) Appl. No.: 16/246,071

(22) Filed: Jan. 11, 2019

(65) Prior Publication Data

US 2019/0142451 A1   May 16, 2019

Related U.S. Application Data

(62) Division of application No. 14/741,126, filed on Jun. 16, 2015, now Pat. No. 10,182,841.

(51) Int. Cl.
*A61B 17/3207* (2006.01)
*A61M 25/10* (2013.01)
*A61B 17/00* (2006.01)

(52) U.S. Cl.
CPC ... *A61B 17/320725* (2013.01); *A61M 25/104* (2013.01); *A61B 2017/00526* (2013.01); *A61M 25/1029* (2013.01); *A61M 2025/105* (2013.01); *A61M 2025/109* (2013.01); *A61M 2025/1079* (2013.01); *A61M 2025/1086* (2013.01)

(58) Field of Classification Search
CPC ........ A61M 25/104; A61M 2025/1086; A61M 2025/105; A61M 2025/1079; A61M 2025/109; A61M 25/1029; A61M 25/1024; A61M 25/1027; A61M 2025/1031; A61B 17/320725; A61B 2017/00526; A61B 2017/22001; A61B 2017/22067; A61B 2017/22068; A61B 2017/22069

See application file for complete search history.

(56) References Cited

U.S. PATENT DOCUMENTS

| | | | | | |
|---|---|---|---|---|---|
| 4,762,130 | A | * | 8/1988 | Fogarty | A61M 25/1002 606/159 |
| 5,102,402 | A | * | 4/1992 | Dror | A61F 2/958 604/103.02 |
| 5,196,024 | A | * | 3/1993 | Barath | A61B 17/320725 604/103.07 |
| 5,320,634 | A | * | 6/1994 | Vigil | A61B 17/320725 604/103.08 |
| 5,470,313 | A | * | 11/1995 | Crocker | A61M 25/1002 604/103.07 |
| 5,792,158 | A | * | 8/1998 | Lary | A61B 17/320725 604/22 |
| 5,797,935 | A | * | 8/1998 | Barath | A61B 17/320725 606/159 |

(Continued)

*Primary Examiner* — Phong Son H Dang
(74) *Attorney, Agent, or Firm* — Dickinson Wright PLLC; Andrew D. Dorisio

(57) ABSTRACT

A balloon includes a plurality of radial projections formed in a working surface for use in providing a focused force during the angioplasty procedure. The plurality of radial projections may be formed in a wall of the balloon and spaced apart in a longitudinal direction. The projections for use in connection with such a balloon may comprise wires or wire segments, and may also comprise radiopaque materials to facilitate viewing under fluoroscopy during the procedure. Related methods of manufacturing are also disclosed.

11 Claims, 6 Drawing Sheets

(56) References Cited

U.S. PATENT DOCUMENTS

| | | | |
|---|---|---|---|
| 6,129,706 A * | 10/2000 | Janacek | A61M 25/1002 604/103.08 |
| 6,409,652 B1 * | 6/2002 | Kamdar | A61N 5/1002 600/3 |
| 6,450,988 B1 * | 9/2002 | Bradshaw | A61N 5/1002 600/3 |
| 6,632,231 B2 * | 10/2003 | Radisch, Jr. | A61B 17/320725 606/159 |
| 7,008,438 B2 * | 3/2006 | O'Brien | A61M 25/04 604/103.08 |
| 7,291,158 B2 * | 11/2007 | Crow | A61B 17/320725 606/159 |
| 7,309,324 B2 * | 12/2007 | Hayes | A61M 25/104 604/96.01 |
| 7,354,419 B2 * | 4/2008 | Davies, Jr. | A61M 25/10 604/103.06 |
| 7,494,497 B2 * | 2/2009 | Weber | A61B 17/320725 606/159 |
| 7,691,119 B2 * | 4/2010 | Farnan | A61M 25/104 606/194 |
| 8,043,259 B2 * | 10/2011 | Radisch, Jr. | A61L 29/126 604/103.08 |
| 8,066,726 B2 * | 11/2011 | Kelley | A61B 17/320725 606/159 |
| 8,070,729 B2 * | 12/2011 | Solar | A61M 25/104 604/164.13 |
| 8,211,354 B2 * | 7/2012 | Burton | A61B 17/320725 264/532 |
| 8,323,325 B2 * | 12/2012 | Valencia | A61M 25/1002 623/1.11 |
| 8,348,987 B2 * | 1/2013 | Eaton | A61M 25/104 623/1.11 |
| 8,361,096 B2 * | 1/2013 | Bence | A61B 17/320725 606/159 |
| 8,454,637 B2 * | 6/2013 | Aggerholm | A61B 17/320725 606/159 |
| 8,585,959 B2 * | 11/2013 | Burton | A61M 25/104 264/532 |
| 8,945,160 B2 * | 2/2015 | Krolik | A61F 2/958 606/159 |
| 9,586,031 B2 * | 3/2017 | Konstantino | A61M 25/104 |
| 10,232,148 B2 * | 3/2019 | Konstantino | A61M 25/104 |
| 10,471,238 B2 * | 11/2019 | Schneider | A61M 25/1029 |
| 2002/0010489 A1 * | 1/2002 | Grayzel | A61F 2/958 606/194 |
| 2002/0029015 A1 * | 3/2002 | Camenzind | A61B 17/320725 604/97.02 |
| 2002/0183777 A1 * | 12/2002 | Shannon | A61M 25/104 606/192 |
| 2003/0014100 A1 * | 1/2003 | Maria Meens | A61F 2/82 623/1.11 |
| 2003/0163148 A1 * | 8/2003 | Wang | A61B 17/320725 606/159 |
| 2005/0021071 A1 * | 1/2005 | Konstantino | A61M 25/104 606/194 |
| 2005/0038383 A1 * | 2/2005 | Kelley | A61B 17/320725 604/103.06 |
| 2005/0038504 A1 * | 2/2005 | Halleriet | A61P 9/08 623/1.42 |
| 2005/0080478 A1 * | 4/2005 | Barongan | A61B 17/320725 623/1.14 |
| 2005/0119678 A1 * | 6/2005 | O'Brien | A61B 17/320758 606/159 |
| 2005/0149082 A1 * | 7/2005 | Yee | A61M 25/1002 606/159 |
| 2005/0228343 A1 * | 10/2005 | Kelley | A61M 25/1027 604/96.01 |
| 2005/0240147 A1 * | 10/2005 | Makower | A61B 17/3201 604/96.01 |
| 2005/0288629 A1 * | 12/2005 | Kunis | A61M 25/104 604/96.01 |
| 2006/0149308 A1 * | 7/2006 | Melsheimer | A61B 17/320725 606/192 |
| 2006/0184191 A1 * | 8/2006 | O'Brien | A61M 25/1002 606/192 |
| 2008/0033477 A1 * | 2/2008 | Campbell | A61M 25/104 606/194 |
| 2008/0125805 A1 * | 5/2008 | Mische | A61B 17/7258 606/196 |
| 2008/0140176 A1 * | 6/2008 | Krause | A61F 2/91 623/1.11 |
| 2008/0180221 A1 * | 7/2008 | Tuttle | G06K 19/0723 340/10.2 |
| 2008/0228139 A1 * | 9/2008 | Melsheimer | A61M 25/104 604/103.08 |
| 2008/0306440 A1 * | 12/2008 | Hirszowicz | A61M 29/02 604/99.01 |
| 2008/0306441 A1 * | 12/2008 | Brown | A61M 25/10 604/99.01 |
| 2009/0038752 A1 * | 2/2009 | Weng | A61M 25/104 156/276 |
| 2009/0054805 A1 * | 2/2009 | Boyle, Jr. | A61B 17/320016 600/564 |
| 2009/0105687 A1 * | 4/2009 | Deckman | A61P 9/00 604/509 |
| 2009/0234283 A1 * | 9/2009 | Burton | A61B 17/320725 604/103.08 |
| 2009/0240270 A1 * | 9/2009 | Schneider | A61M 25/104 606/159 |
| 2009/0281490 A1 * | 11/2009 | McAuley | A61M 25/10 604/103.08 |
| 2009/0299327 A1 * | 12/2009 | Tilson | A61M 25/0147 604/500 |
| 2009/0318863 A1 * | 12/2009 | Chen | A61M 25/10 604/103.01 |
| 2010/0022950 A1 * | 1/2010 | Anderson | A61B 18/1492 604/100.01 |
| 2010/0036410 A1 * | 2/2010 | Krolik | A61M 25/1011 606/194 |
| 2010/0042198 A1 * | 2/2010 | Burton | A61M 25/1011 623/1.11 |
| 2011/0082483 A1 * | 4/2011 | Diamant | A61B 17/320725 606/159 |
| 2011/0208285 A1 * | 8/2011 | Stockert | A61F 2/958 623/1.11 |
| 2012/0035701 A1 * | 2/2012 | To | A61F 2/958 623/1.11 |
| 2012/0059401 A1 * | 3/2012 | Konstantino | A61M 25/104 606/159 |
| 2012/0109057 A1 * | 5/2012 | Krolik | A61B 17/32053 604/103.01 |
| 2012/0143054 A1 * | 6/2012 | Eaton | A61M 25/104 600/435 |
| 2013/0053768 A1 * | 2/2013 | Hennessey | A61M 25/104 604/96.01 |
| 2013/0261547 A1 * | 10/2013 | Aggerholm | B29C 49/04 604/103.06 |
| 2014/0324079 A1 * | 10/2014 | Silvestro | A61B 17/32075 606/159 |
| 2015/0100079 A1 * | 4/2015 | Moffarah | A61B 17/320725 606/194 |
| 2016/0374715 A1 * | 12/2016 | McPeak | A61B 17/320725 606/159 |
| 2017/0007805 A1 * | 1/2017 | Tsubooka | A61B 17/22 |
| 2017/0150988 A1 * | 6/2017 | Konstantino | A61M 5/00 |
| 2018/0099126 A1 * | 4/2018 | Rousu | A61M 25/1002 |

* cited by examiner

MEDICAL BALLOON WITH ENHANCED FOCUSED FORCE CONTROL

This application is a divisional of U.S. application Ser. No. 14/741,126 filed on Jun. 16, 2015, which is incorporated herein by reference.

TECHNICAL FIELD

This disclosure relates generally to interventional medical procedures, such as angioplasty, and, more particularly, to a medical balloon including radial projections for providing a focused force.

BACKGROUND

Balloon dilatation catheters are used to treat lesions in vessels. However, difficulties are encountered in navigating tortuous anatomy and safely crossing very tight lesions. Moreover, some lesions are difficult to crack using just a balloon, and require a focused force to enable cracking of the lesion at safe inflation pressures. In the past, others have proposed balloons with external wires for providing a focused force, such as in U.S. Pat. No. 8,070,729, the disclosure of which is incorporated herein by reference. The proposal for exposed wires (such as a core wire and a guide wire) adds to the manufacturing complexity. The specific locations required for the wires (which are asymmetrical in the proposed design of the '729 patent) and the full extension along the balloon also dictates the location or direction of the focused force provided, which contributes to a lack of control over these parameters.

Accordingly, a need is identified for a balloon and related dilatation catheter with enhanced flexibility in controlling the application of a focused force, such as for scoring or cracking lesions, and which can be manufactured in a simpler manner than past proposals.

SUMMARY

In one aspect, this disclosure pertains to an apparatus for performing an angioplasty procedure. The apparatus comprises a balloon including a plurality of radial projections for use in providing a focused force during the angioplasty procedure. The plurality of radial projections are spaced apart from each other in a longitudinal direction.

In one possible embodiment, the plurality of radial projections each comprise a wire positioned between first and second layers of a wall of the balloon, such as along a central or barrel section of the balloon. These radial projections may align in the longitudinal direction, and may be spaced apart in the circumferential direction. The projections may be adapted to be viewed under fluoroscopy and, thus at least one of the radial projections may comprise a radiopaque material, and may be adapted to expand in the longitudinal direction.

The radial projections may be symmetrically arranged about a longitudinal axis of the balloon. The projections may also be symmetrical about a transverse axis of the balloon. Three or more projections may be provided, and a catheter shaft may be connected to the balloon for providing guidance and serving as a conduit for inflation fluid during the procedure.

According to another aspect of the disclosure, an apparatus for performing an angioplasty procedure is provided. The apparatus comprises a balloon including a first radial projection embedded in a wall of the balloon and extending in a longitudinal direction. The first radial projection may be at least partially radiopaque.

In one embodiment, the first radial projection comprises a first wire, which wire may comprise a radiopaque material. A second radial projection may also be embedded in the wall of the balloon, and also may comprise a radiopaque material. The second radial projection may comprise a wire, and may be aligned with the first radial projection in the longitudinal direction. The first and second radial projections may be spaced apart in the longitudinal direction, the circumferential direction, or both such directions. A third radial projection may be embedded in the wall of the balloon. The first and second radial projections may be symmetrical about a longitudinal axis of the balloon, which may be attached to a catheter shaft for use in the angioplasty procedure.

A related aspect of the disclosure comprises a method of manufacturing a medical balloon. The method comprises providing an inflated base balloon, and attaching one or more wires (including possibly wire segments, and also radiopaque wires) to an outer surface of the base balloon, such as along a generally cylindrical central or barrel section. The method may further include the step of providing a cover for covering the wires. The one or more wires may be attached to the cover prior to the attaching step. The method may further include the step of attaching the base balloon in a deflated state to a catheter shaft, such as after the wires are attached to it.

DETAILED DESCRIPTION

The description provided below and in regard to the figures applies to all embodiments unless noted otherwise, and features common to each embodiment are similarly shown and numbered.

Figure 1:
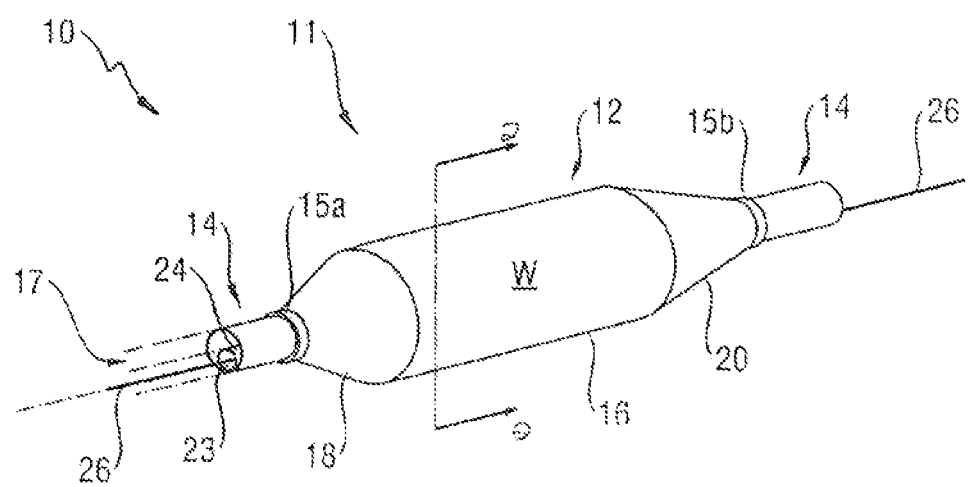
FIG. 1 is a perspective view of a catheter and balloon according to an embodiment disclosed herein.
Figure 2:
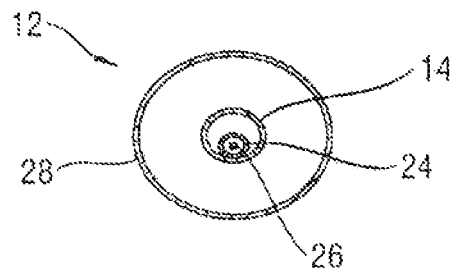
FIG. 2 is a cross-section of the balloon of FIG. 1 along line 2-2.
Figure 3:
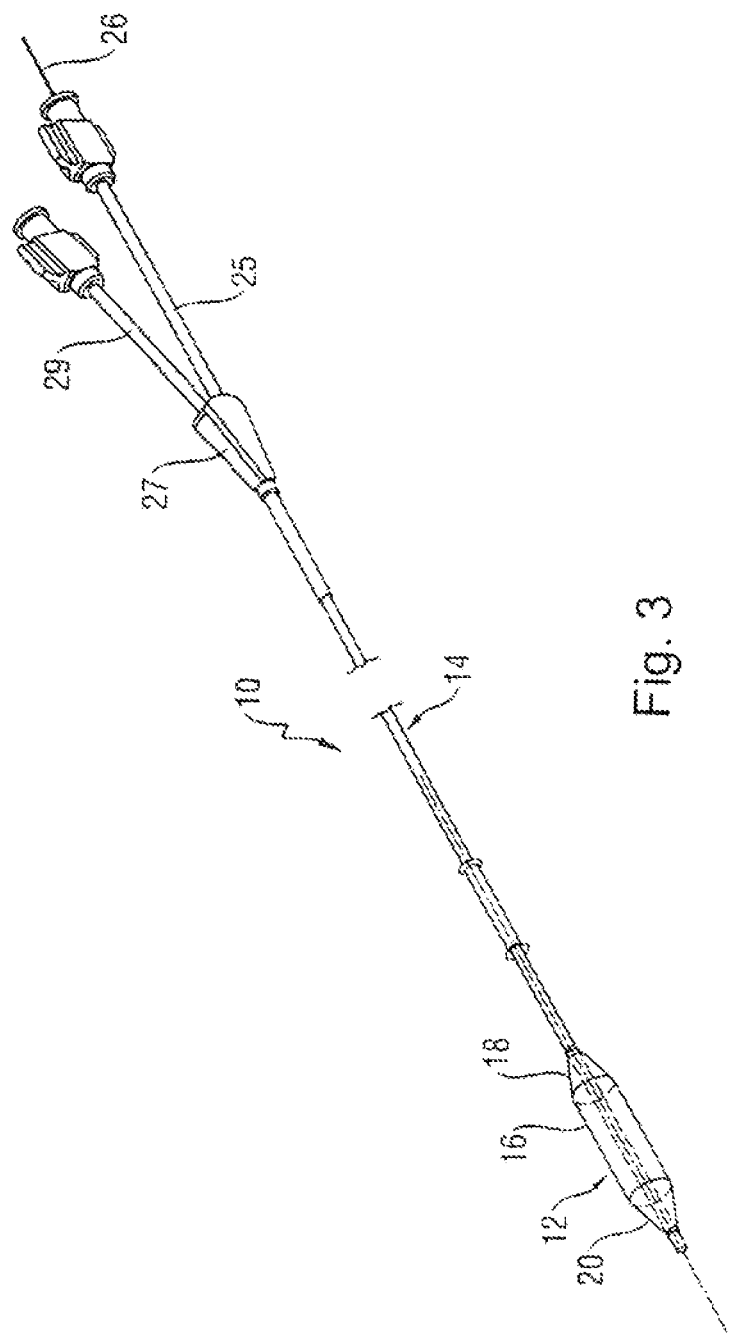
FIG. 3 is a further perspective of the catheter and balloon according to an embodiment disclosed herein.

Provided is a catheter structure in the form of a tubular catheter 10 capable of being actuated in some manner in order to provide a treatment. In this one example for purposes of illustration, the catheter 10 includes a distal portion 11 with an actuatable or inflatable element in the form of a balloon 12 mounted on a catheter tube 14. Referring to FIGS. 1, 2, and 3, the balloon 12 has an intermediate section 16, or "barrel," having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
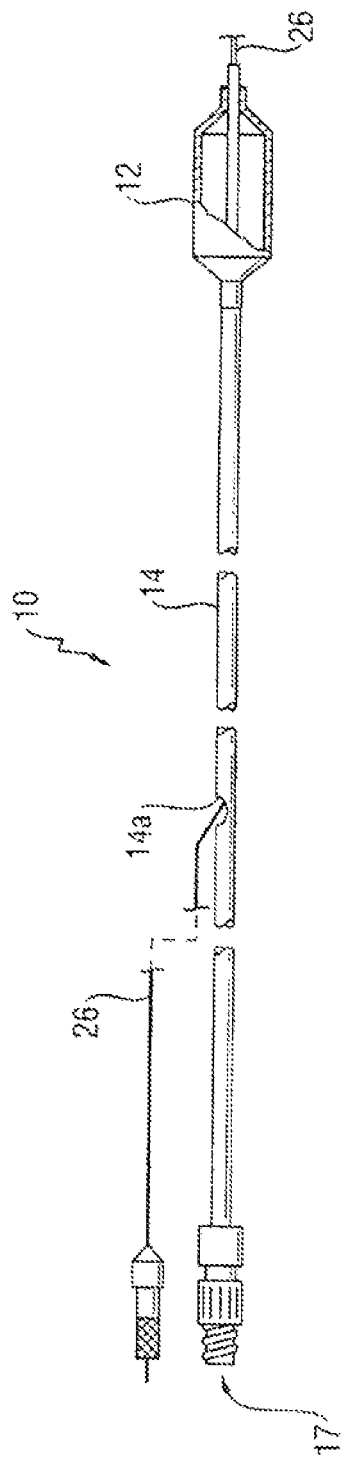
FIG. 4 is an elevational view of a catheter and guidewire according to a further embodiment disclosed herein.

The catheter tube 14 also includes an elongated, tubular shaft 24 forming a lumen 23 that directs another catheter structure, such as guidewire 26, through the catheter 10. As illustrated in FIG. 3, this guidewire 26 may be inserted through a first port 25 of a connector 27, such as a hub, into the lumen 23 to achieve an "over the wire" (OTW) arrangement, but could also be provided in a "rapid exchange" configuration in which the guidewire 26 enters the lumen through a lateral opening 14a closer to the distal end (see FIG. 4). A second port 29 may also be associated with catheter 10, such as by way of connector 27, for introducing a fluid (e.g., saline, a contrast agent, or both) into the interior of the balloon 12 via the inflation lumen 17.

The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use.

In connection with one aspect of the disclosure, and with reference to FIGS. 5-8, the balloon 12 may be provided with a plurality of focused force elements in the nature of projections 30. The projections 30 extend radially in connection with the working surface W of the balloon 12 when inflated, which surface but for the projections thus has a lesser diameter (as can be understood from FIG. 6a, with diameters D1 and D2, where D2>D1). Hence, by the term "radial projection," it is meant that the projection 30 extends above a surface of the balloon 12 associated with a nominal diameter when inflated and, thus, is intended for providing a focused force, such as for treating a lesion during an angioplasty procedure.

Figure 5:
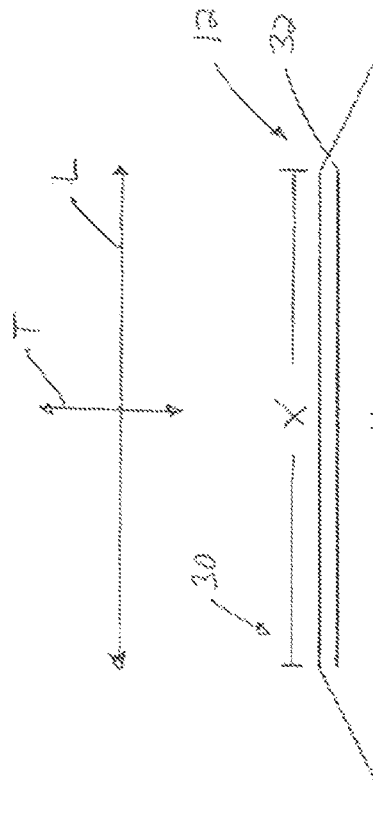
FIG. 5 is a schematic side view of one possible embodiment.
Figure 6:
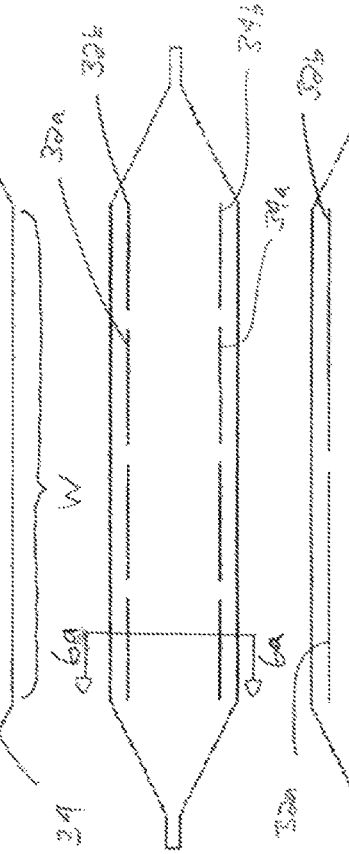
FIGS. 6 and 6*a* are schematic side and cross-sectional views, respectively, of an alternate embodiment.
Figure 7:
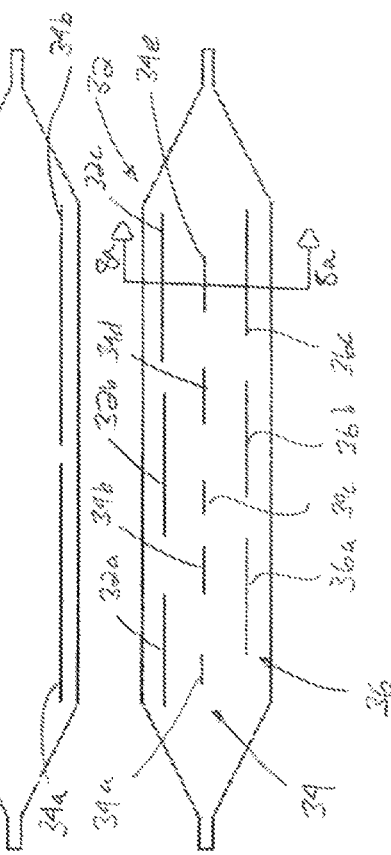
FIG. 7 is a schematic side view of one alternate embodiment.
Figure 8:
FIGS. 8 and 8*a* are schematic side and cross-sectional views, respectively, of an alternate embodiment.

As shown in FIG. 5, the one or more of the projections 30 may comprise an elongated wire, which may have a dimension X in the longitudinal direction L that substantially corresponds to the working surface W of the central or barrel section 16 of the balloon 12. However, as can be understood from FIGS. 6-8, individual wires forming the radial projections 30 may be aligned, but spaced apart, in the longitudinal direction L. In other words, each projection 30, such as wires 32, 34, may comprise a plurality of wire segments 32a, 32b; 34a, 34b, together extending along the length of the balloon 12. The spacing of the segments 32a, 32b may be close, as shown in FIG. 6, and may be regular, as shown in FIGS. 6 and 7, but may be irregular, as shown in FIG. 8. Different wires may also be provided as different numbers of wire segments (see, e.g., FIG. 8, wires 32 and 34 have three segments each, 32a-32c and 34b-34c, whereas wire 36 has five segments, 36a-36e, but any number may be used depending on the particular application). In any case, it can be appreciated that the strategic positioning of the wires or wire segments allows for greater control of the focused force provided on inflation of the balloon 12 in the vasculature, such as for scoring a lesion.

Figure 6A:
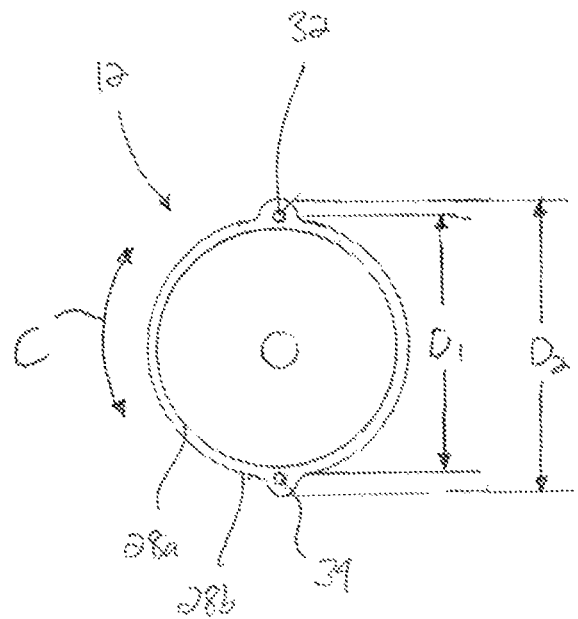
Figure 8A:
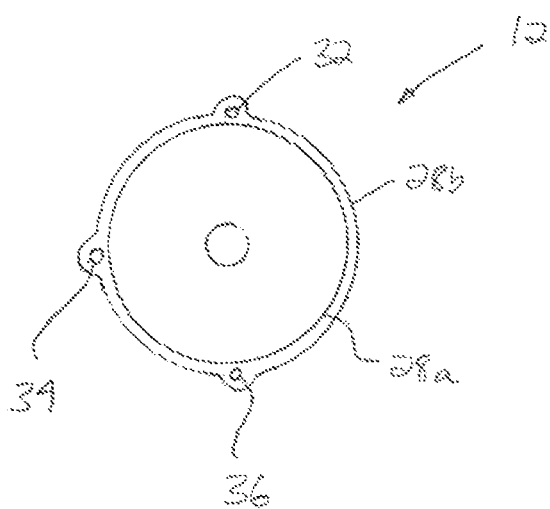

With reference to FIGS. 5-8, the projections 30 may be provided in a manner such that the balloon 12 (and the balloon wall 28 in particular) has a degree of symmetry about at least a longitudinal axis (note first wire 32 and second wire 34 in FIG. 5, which are offset in the circumferential direction C by 180 degrees, as can be seen in FIG. 6a). Hence, as can be appreciated, the projections 30 extend generally parallel to each other. Symmetry of the balloon 12 or wall 28 may also be provided about a transverse axis T, as shown in FIGS. 6 and 7 (as well as about the longitudinal axis or otherwise). However, it can be understood from FIGS. 8 and 8a that this symmetry is optional. Indeed, the projections 30 may be provided such that the balloon 12 has a scoring portion or face, and a non-scoring portion or face.

Figure 9:
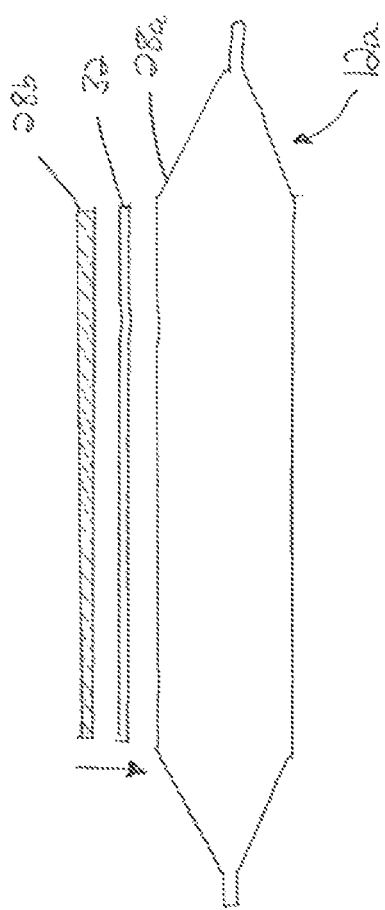
FIGS. 9 and 10 illustrate aspects of possible manufacturing techniques.

In one particular embodiment according to the disclosure, and with reference to FIG. 5a, the projections 30 may be embedded between layers of the balloon wall 28, such as a base layer 28a and a cover or covering, such as a second layer, such as outer layer 28b, and thus remain captured in place during use. In one possible version, and with reference to FIG. 9, the balloon 12 may be manufactured by attaching the wire 32, wires or wire segments to the base layer 28a. This may be done after forming the base layer 28a into a base balloon and inflating it to form balloon 12, and then attaching the outer layer 28b to form the balloon wall 28 with the embedded wires or segments. The attachment can be made using adhesives, heat (e.g., laser welding), pressure, or any suitable bonding techniques. The outer layer 28b may be applied using a film, or by spray coating, dipping, or other technique for material deposition (including possibly vapor deposition).

Figure 10:
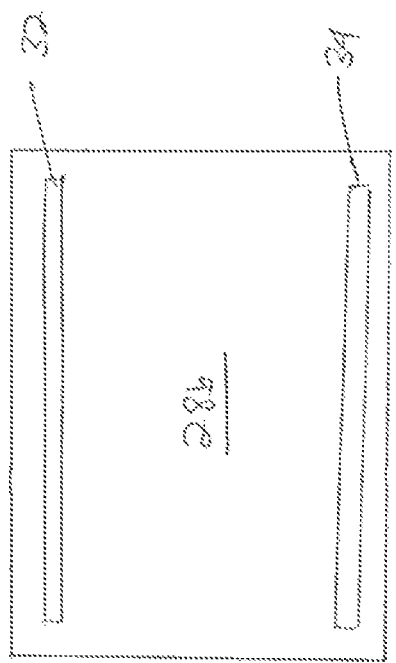

Alternatively, the wires or segments could also be first attached to the outer layer 28b, such as by way of an adhesive, or possibly by being embedded between layers of material forming the outer layer 28b) to form a sheet, as shown in FIG. 10. This outer layer 28b with the wires or segments attached (note wires 32, 34) may then be placed over all or part of the base layer 28a, such as by wrapping the layer 28b around the inflated balloon precursor 12a with an interposed adhesive, and possibly using heat or pressure. Additional layers may also be provided to form balloon wall 28, and the wires or wire segments may be arranged between different layers of the balloon wall (e.g., wire 32 could be between base layer 28a and an intermediate layer (not shown), and wire 34 could be between that intermediate layer and outer layer 28b). In any case, the resulting balloon 12 may be deflated, attached to a catheter shaft (if not already done) and folded, once the construction is completed.

The wire or wire segments may be made of various materials, and may each be made of the same materials or materials with similar material properties, or different materials having different properties. As one example, the wires or wire segments may be formed of stainless steel. The material used should be stiffer than the materials forming the layers 28a, 28b of the balloon wall 28 to thus ensure that the desired scoring function is achieved.

In one embodiment, the wires or wire segments comprise a material that is radiopaque (either a homogeneous material or a material that is non-radiopaque and provided with a radiopaque coating), and thus visible under fluoroscopy. Radiopaque markers, such as bands, could also be attached to the wires or wire segments forming the projections. Thus, when the wires correspond to the working surface W of the balloon 12, this allows the clinician to understand the length of this surface when the balloon is under fluoroscopy. Making the projections visible may also allow the clinician to better understand the orientation of the balloon 12 in the vasculature, as well as the positioning of the balloon in the course of applying the focused force to a lesion.

The wire or wire segments forming the projections 30 may also have any cross-sectional shape, including for example, circular, square, or triangular, and different projections may have different cross-sectional shapes. Rounded shapes or smooth edges would help to prevent the wire or wire segment forming the projection 30 from perforating the covering or outer layer 28b of the balloon wall 12. The degree of projection in the radial direction may also be varied by changing the corresponding dimension of the wire or wire segment, or possibly by creating an accommodating pocket or recess in the base layer 28a.

Examples of radiopaque materials include, but are not limited to, finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The amount used may vary depending on the desired degree of radiopacity.

The wire or wire segments may also be made of a material capable of expanding in at least the longitudinal direction when the balloon 12 is inflated. In the case of a wire, this may be achieved by making the wire in a spiral configuration, and thus essentially forming a spring. However, it may also be possible to fabricate the wires or segments from materials that are elastic, as well as materials that have a shape memory (e.g., Nitinol), to achieve the desired expansion and retraction during inflation/deflation. The balloon 12 may be formed of any known materials suitable for forming inflatable medical balloons (e.g., Nylon-12, PEBAX, etc.) and may further include reinforcements, such as fibers, to increase the burst pressure.

The balloon 12 may also be provided with a treatment in the nature of a pharmaceutical or drug. Examples of such compounds include rapamycxin or paclitaxel. The projections 30 may also be associated with the pharmaceutical or drug, and thus serve to identify its location on the balloon 12.

While the disclosure presents certain embodiments to illustrate the inventive concepts, numerous modifications, alterations, and changes to the described embodiments are possible without departing from the sphere and scope, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the terms "approximately," "generally," or "substantially" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. A method of manufacturing a medical balloon, comprising:
   providing an inflated base balloon including a generally cylindrical section; and
   fixedly attaching one or more wires to an outer surface of the base balloon along the generally cylindrical section to form one or more radial projections in a working surface of the medical balloon for providing a focused force when the medical balloon is used in connection with an angioplasty procedure; and
   providing a cover for covering the wires;
   wherein the one or more wires is attached to the cover prior to the attaching step.

2. The method of claim 1, further including the step of attaching the base balloon in a deflated state to a catheter shaft.

3. The method of claim 1, wherein the attaching step comprises attaching one or more radiopaque wires to the outer surface of the balloon.

4. A method of manufacturing a medical balloon, comprising:
   providing an inflated base balloon including a generally cylindrical section; and
   fixedly attaching one or more wires to an outer surface of the base balloon along the generally cylindrical section to form one or more radial projections in a working surface of the medical balloon for providing a focused force when the medical balloon is used in connection with an angioplasty procedure; and
   providing a fixed cover for covering the wires and embedding the one or more wires between the inflated base balloon and the fixed cover.

5. The method of claim 4, wherein the one or more wires is attached to the cover prior to the attaching step.

6. The method of claim 4, further including the step of attaching the base balloon in a deflated state to a catheter shaft.

7. The method of claim 4, wherein the attaching step comprises attaching one or more radiopaque wires to the outer surface of the balloon.

8. A method of manufacturing a medical balloon, comprising:
   providing an inflated base balloon including a generally cylindrical section between two cone sections; and
   fixedly attaching one or more wires to an outer surface of the base balloon along the generally cylindrical section to form one or more radial projections in a working surface of the medical balloon for providing a focused force when the medical balloon is used in connection with an angioplasty procedure; and
   providing a cover for covering the wires;
   wherein the one or more wires extend in a longitudinal direction no greater than a longitudinal length of the cylindrical section of the base balloon.

9. The method of claim 8, wherein the one or more wires is attached to the cover prior to the attaching step.

10. The method of claim 8, further including the step of attaching the base balloon in a deflated state to a catheter shaft.

11. The method of claim 8, wherein the attaching step comprises attaching one or more radiopaque wires to the outer surface of the balloon.

\* \* \* \* \*